US012558455B2

(12) United States Patent
Ganey et al.

(10) Patent No.: US 12,558,455 B2
(45) Date of Patent: Feb. 24, 2026

(54) BIOLOGIC COMPOSITION AND METHOD OF USE

(71) Applicant: Vivex Biologics Group, Inc., Atlanta, GA (US)

(72) Inventors: Timothy Ganey, Tampa, FL (US); Shabnam Namin, Miami, FL (US); Harry Thomas Temple, Miami, FL (US)

(73) Assignee: Vivex Biologics Group, Inc., Atlanta, GA (US)

( * ) Notice: Subject to any disclaimer, the term of this patent is extended or adjusted under 35 U.S.C. 154(b) by 0 days.

(21) Appl. No.: 17/114,896

(22) Filed: Dec. 8, 2020

(65) Prior Publication Data

US 2021/0178020 A1     Jun. 17, 2021

Related U.S. Application Data

(60) Provisional application No. 62/947,705, filed on Dec. 13, 2019.

(51) Int. Cl.
*A61L 27/36*     (2006.01)
*A61M 5/32*     (2006.01)

(52) U.S. Cl.
CPC ....... *A61L 27/3608* (2013.01); *A61L 27/3604* (2013.01); *A61L 27/365* (2013.01); *A61M 5/329* (2013.01); *A61L 2300/214* (2013.01); *A61L 2300/252* (2013.01); *A61L 2300/258* (2013.01); *A61L 2300/802* (2013.01); *A61L 2400/06* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 9,675,643 B2 | 6/2017 | Weston | |
| 9,687,511 B2 | 6/2017 | Weston | |
| 2003/0220696 A1* | 11/2003 | Levine | A61L 27/06 |
| | | | 607/51 |
| 2007/0116682 A1 | 5/2007 | Atala et al. | |
| 2010/0129415 A1* | 5/2010 | Kinnane | A61L 27/3604 |
| | | | 514/9.3 |
| 2010/0228335 A1 | 9/2010 | Schorgl | |
| 2010/0310504 A1* | 12/2010 | Lowe | A61P 43/00 |
| | | | 424/85.5 |
| 2011/0172315 A1* | 7/2011 | Matsumura | A23L 3/375 |
| | | | 426/442 |
| 2013/0344162 A1 | 12/2013 | Morse | |
| 2016/0158291 A1 | 6/2016 | Kreke | |
| 2016/0213714 A1* | 7/2016 | Gudkov | A61K 35/13 |
| 2017/0136071 A1 | 5/2017 | Danilkovitch et al. | |

FOREIGN PATENT DOCUMENTS

| | | |
|---|---|---|
| WO | 2015016761 | 2/2015 |

OTHER PUBLICATIONS

Meng et al. The American Journal of Pathology, vol. 185, No. 3, Mar. 2015. (Year: 2015).*
Iijima et al., ACS Omega 2018, 3, 10180-10187 (Year: 2018).*
Novak et al., The Journal of Immunology, 2020, 204: 868-878 (Year: 2020).*
Zhu et al Nature Communications (2019) 10:4620, 14 pages; (Year: 2019).*
Li et al., Journal of Biomaterials Applications 2018, vol. 33(2), pp. 182-195 (Year: 2018).*
Li et al., Immunosuppressive Factors Secreted by Human Amniotic Epithelial Cells, Investigative Ophthalmology & Visual Science, Mar. 2005, vol. 46, No. 3, pp. 900-907.
Luo et al., Human Villous Trophoblasts Express and Secrete Placenta-Specific MicroRNAs into Maternal Circulation via Exosomes, Biology of Reproduction, vol. 81, pp. 717-729 (2009).
Sheller et al., Amnion-Epithelial-Cell Derived Exosomes Demonstrate Physiologic State of Cell under Oxidative Stress, PLOS One, Jun. 22, 2016, pp. 1-25.
Salomon et al., PLOS One, Jul. 2013, vol. 8, Issue 7, e68451, pp. 1-24.
Zhang et al.,Stem Cells, 2015; 33: 2158-2168.
Matsumura et al Cell Transplantation, vol. 19, pp. 691-699, 2010.
Weston et al., BioDrugs (2019) 33: 137-158.
Dai et al., Diabetes, 2018; 67: 2154-2156.
Blake et al., American Journal of Pathology, vol. 155, No. 1, Jul. 1999, pp. 67-70.
Chow et al., Cytokine, vol. 44 (2008), pp. 78-84.
Crouch etal., J. Cell Biology vol. 78, pp. 701-715, 1978.
Keller et al., Kidney International (2007) vol. 72, pp. 1095-1102.
Lu etal., Obstetrics & Gynecology, vol. 94, No. Jul. 1, 1999, pp. 7-10.
Maraldi et al., Tissue Engineering: Part A, vol. 17, Nos. 21 and 22, 2011, pp. 2833-2843.
Mesavage et al., Pediatric Research, vol. 19, No. 10, 1985, pp. 1021-1024.
Perluigi et al., Journal of Prenatal Medicine, 2009; vol. 3, No. 3: pp. 39-41.
Watkins et al., Annals of Clinical and Laboratory Science, vol. 7, No. 3, 1977, pp. 231-240.

(Continued)

*Primary Examiner* — Evelyn Y Pyla
(74) *Attorney, Agent, or Firm* — Kilpatrick Townsend & Stockton LLP

(57)     ABSTRACT

A biologic composition responsive to inflammation has an allograft scaffold matrix for injection or implantation. The allograft scaffold matrix has donor quiescent and/or senescent cells. The donor quiescent and/or senescent cells react in response to signaling of inflammation from host cells or matrix. The reaction to signaling causes the donor quiescent and/or senescent cells to secrete anti-inflammatory cytokines and secrete exosomes to initiate regeneration of the area of the inflammation. The biologic composition further has a cryoprotectant. The cryoprotectant is a polyampholyte, preferably the polyampholyte is an ε-poly-L-lysine. The cryoprotectant is not DMSO or glycerol based. The cryoprotectant is suitable for direct implantation without washing from the allograft scaffold matrix in either a diluted or non-diluted state.

25 Claims, 5 Drawing Sheets

(56)        References Cited

OTHER PUBLICATIONS

Weber et al., Clin Chem, Nov. 2010; vol. 56, No. 11; pp. 1733-1741.
Salomon et al., PLOS One, Jun. 2014, vol. 9, Issue 6 e98667, pp.
1-12.
Zhang, An; Cytokines, Inflammation and Pain, Int Anesthesiol Clin
2007, Spring; 45(2): 27-37.

* cited by examiner

Donor Cells
Plus Matrix Scaffold

Host cells
Degenerate matrix

Donor Cells
Plus Matrix Scaffold

Host cells
Degenerate matrix

BIOLOGIC COMPOSITION AND METHOD OF USE

CROSS-REFERENCE TO RELATED APPLICATIONS

This application claims priority to U.S. Provisional Application No. 62/947,705, filed Dec. 13, 2019, the entire disclosure of which is incorporated herein by reference.

TECHNICAL FIELD

This invention is a tissue regenerative biologic composition. More specifically, an allograft scaffold matrix including senescent cells with a cryoprotectant.

BACKGROUND OF THE INVENTION

The use of stem cells in compositions for use in therapeutic treatments has been commonly accepted. Maintaining the viability of these cells from recovery to processing and storage has been a challenge. Various cryoprotectants have been used to preserve the cells. Many, with DMSO and other glycerol-based products in particular require the protectant to be washed away prior to implanting the cells to protect the cells and avoid inherent toxicity accounted to latent exposure. Such extended exposure often leads to huge loss of viable cells available from the initial amount of cells transplanted, with individual conditions due to patient variation not affording a predictable response. Accordingly, the outcomes for patients can vary widely.

In U.S. Pat. No. 9,675,643, a way to protect the cell was discovered using a polyampholyte carboxylated e-polylysine-based protectant suitable for direct implantation without washing.

In a related patent, U.S. Pat. No. 9,687,511, it was discovered such a protectant could be used to protect acellular compositions.

In the present invention, a new method and composition has been discovered that employs donor quiescent and/or senescent cells that preferably are treated with DMSO-free protectants that can be used, cryopreserved, stored, frozen and when thawed and implanted maintained an ability to respond to signals of inflammation from host cells. Importantly, the composition can be tuned to exhibit different cell stimulating properties to enhance its performance when implanted.

The following compositions and methods described herein form the basis of the present invention.

SUMMARY OF THE INVENTION

A biologic composition responsive to inflammation has an allograft scaffold matrix for injection or implantation. The allograft scaffold matrix has donor quiescent and/or senescent cells. The donor quiescent and/or senescent cells react in response to signalling of inflammation from host cells during placement. The reaction by these cells to signalling causes the donor quiescent and/or senescent cells to secrete anti-inflammatory cytokines and secrete appropriate cytokines and exosomes to counteract inflammation and initiate regeneration of the area affected by inflammation. The biologic composition further has a cryoprotectant. The cryoprotectant is a polyampholyte, preferably the polyampholyte is an ε-poly-L-lysine. The cryoprotectant is not DMSO or glycerol based. The cryoprotectant is suitable for direct implantation without washing from the allograft scaffold matrix in either a diluted or non-diluted state.

The donor quiescent and/or senescent cells can be derived from bone marrow or placental tissue.

In one embodiment, the allograft scaffold matrix further has allograft bone in the form of chips, fibers or particles or any combination thereof. The allograft bone further may be mineralized, demineralized, partially demineralized, surface demineralized, or appropriate combinations of mineralized and demineralized bone chips, fibers or particles or any combination thereof.

In another embodiment, the allograft scaffold matrix further has nucleus pulposus particles or fibers or combinations thereof. The nucleus pulposus particles or fibers can be freeze-dried. The freeze-dried nucleus pulposus particles or fibers have been hydrated in the scaffold matrix with saline, and can be delivered in suspension as well with hydration occurring in situ. Preferably, the freeze-dried nucleus pulposus particles or fibers are micronized to be 400 microns or less. More preferably, the micronized freeze-dried nucleus pulposus particles or fibers are 300 microns or less and suitable for injection via a small gauge lumen or cannula. The small gauge lumen or cannula is a 22-gauge needle.

The biologic composition reacts to inflammation with a potency that exceeds that of a single molecule. From the perspective of inflammation, each subtle difference in anatomy, each genotypic variability, and individual metabolic states combine to create an infinitesimal architecture of biologic equilibrium that would be impossible to address as a singular mechanism. As such the potency of the biologic support is intended to be responsive to those individual conditions and not titered to an intention that is targeting treatment to an indefinitely small population that is likely singular and variable. The biologic composition can be one or more of mesoderm, endoderm, or ectoderm or combinations thereof exhibiting a broad range of phenotypes. The donor senescent cells can be from a non-marrow derived source and preferring a spine space. Preferably, the donor senescent cells form a heterogenous cell population paradoxically display sufficiently static identity to be calibrated but adequately dynamic responses to balance immune response, antigen presentation, cell survival, cell migration, cell differentiation and angiogenesis, and such allograft response is necessarily variable and responsive to broad conditions with multiple separate response to a patient's condition. The donor quiescent and/or senescent cells are responsive to interspinous or any presented biologic challenge.

The biologic composition consisting of both liquid and solid substances, intermeshing the miscible, varying in aspect ratio, which might range from spherical, to polygonal, and all variations of shapes natural and defined that constitute roughness demonstrating hydrodynamic and mechanical interposition. Asperities can vary between nodes nearly but also in depth between individual areas or structure. The liquid and solid substances form liquid solid interfaces which afford a balance free to exchange, with diffusion potential and equilibrium interchange between liquid and solid substances, host tissue and host, and host elution fraction and exchange appropriately and infinitely variable to host-donor asymmetry. Preferably, the biologic composition is sufficiently stable to protect the anatomy by volume supplementation while at the same time forming a "cauldron" of or secretion from the signalling exchange The allograft scaffold matrix forms a reaction chamber biologic reactor sufficiently capable of future response that allows and promotes exchange, protects and assimilates assembly of materials between donor and host, and tempers the inflammation inherent to regenerative process.

The biologic composition allows for a unique method of treatment. One being a method of treating and repairing a degenerative condition having the steps of: implanting a viable allograft scaffold matrix having donor quiescent, or senescent cells into a degenerated area exhibiting degeneration and inflammation; wherein the step of implanting causes the donor quiescent and/or senescent cells to receive and react to signalling or signals from host cells indicating inflammation; and causing an activation of the donor quiescent and/or senescent cells in response to the signalling to secrete anti-inflammatory cytokines directed to the host cells to reduce the inflammation and to secrete exosomes to initiate regeneration of the degenerated area. The activation of the donor senescent cells in response to the signalling initiates a biological exchange balancing anabolic and catabolic metabolic processes, wherein the activation of the donor senescent cells in response to the signalling causes secretion and exchange of microvesicles, membrane rafts, miRNA, proteins, growth factors, and/or cytokines. In turn, the activation and exchange enable potential for membrane voltage fluctuations to ensure benefit that supports appropriate cell differentiation and tissue regeneration.

Another method treats degenerative discs. A method of treating and repairing a degenerative intervertebral disc has the steps of: implanting a viable intervertebral disc scaffold matrix having donor quiescent and/or senescent cells into a anatomically deficient degenerative disc demonstrating depleted tissue volume and exhibiting inflammation; wherein the step of implanting causes the donor quiescent and/or senescent cells to receive signalling from host cells indicating inflammation; and causing an activation of the donor quiescent and/or senescent cells in response to the signalling to secrete appropriate anti-inflammatory cytokines directed to the host cells to reduce the inflammation and to secrete exosomes and cytokines to initiate regeneration of nucleus pulposus of the degenerative disc.

It is believed that the cryoprotectant when used during cryo-lyophilization protects during drying to maintain and in some cases enhance the bioavailability of the allograft scaffold matrix.

Definitions

As used herein and in the claims:

Cytokines are cell signaling molecules that aid cell to cell communication in immune responses and stimulate the movement of cells towards sites of inflammation, infection and trauma. Cytokines are small secreted proteins released by cells have a specific effect on the interactions and communications between cells. Cytokine is a general name; other names include lymphokine (cytokines made by lymphocytes), monokine (cytokines made by monocytes), chemokine (cytokines with chemotactic activities), and interleukin (cytokines made by one leukocyte and acting on other leukocytes). Cytokines may act on the cells that secrete them (autocrine action), on nearby cells (paracrine action), or in some instances on distant cells (endocrine action). There are both pro-inflammatory cytokines and anti-inflammatory cytokines.

DNase—Deoxyribonuclease is any enzyme that catalyses the hydrolytic cleavage of phosphodiester linkages in the DNA backbone, thus degrading DNA.

DMEM, DMEM/LG—Dulbecco's Modified Eagle Medium, low glucose. Sterile, with: Low Glucose (1 g/L),

4

Sodium Pyruvate; without: L-glutamine, HEPES (4-(2-hydroxyethyl)-1-piperazineethanesulfonic acid).

DMSO—Dimethyl sulfoxide (DMSO) is an organosulfur compound with the formula $(CH_3)_2SO$. This colorless liquid is an important polar aprotic solvent that dissolves both polar and nonpolar compounds and is miscible in a wide range of organic solvents as well as water.

DPBS—Dulbecco's Phosphate Buffered Saline.

CBT-MIXER—Mixing blade for Cancellous Bone Tumbler Jar.

Cold Media—Media used during the preparation of vertebral bodies for initial processing.

"Cryomill"—The CryoMill is tailored for cryogenic grinding. The grinding jar is continually cooled with liquid nitrogen from the integrated cooling system before and during the grinding process. Thus, the sample is embrittled and the chemical composition is preserved. The liquid nitrogen circulates through the system and is continually replenished from an Autofill system in the exact amount which is required to keep the temperature at −196° C. Powerful impact ball milling results in a perfect grinding efficiency. The Autofill system avoids direct contact with LN2 and makes the operation very safe. Its versatility (cryogenic, wet and dry grinding at room temperature) makes the CryoMill the ideal grinder for quantities up to 20 ml. The grinding jar of the CryoMill performs radial oscillations in a horizontal position. The inertia of the grinding balls causes them to impact with high energy on the sample material at the rounded ends of the grinding jar and pulverize it. The grinding jar is continually cooled with liquid nitrogen from the integrated cooling system before and during the grinding process.

Cryopreserved—Tissue frozen with the addition of, or in a solution containing, a cryoprotectant agent such as glycerol, or dimethylsulfoxide, or carboxylated poly-1-lysine.

"Disc Desiccation"—Disc desiccation is an extremely common degenerative change of intervertebral discs. The incidence climbs with age, and to a large degree a gradual desiccation is a 'normal' part of disc aging. It results from replacement of the hydrophilic glycosaminoglycans within the nucleus pulposus with fibrocartilage.

Freeze-dried/Lyophilized—Tissue dehydrated for storage by conversion of the water content of frozen tissue to a gaseous state under vacuum that extracts moisture.

"Freeze Drying"—Freeze-drying, also known as lyophilization, or cryodesiccation, is a dehydration process typically used to preserve a perishable material or make the material more convenient for transport and stable at room temperatures in an appropriate contained or package. Freeze-drying works by freezing the material and then reducing the surrounding pressure to allow the frozen water in the material to sublimate directly from the solid phase to the gas phase.

"Hypothermic Dehydration"—hypothermic dehydration depends on placing the object at reduced temperatures above freezing point into a high vacuum chamber allowing it to dry to a desired residual moisture level. The result is dried tissue without fissures, microscopic ice crystal distortion and collapse phenomenon.

Mesoderm: One of the three primary germ cell layers, the others being the ectoderm and endoderm. The mesoderm is the middle layer. In the embryo, it differentiates to gives rise to a number of tissues and structures including bone, muscle, connective tissue, and the middle layer of the skin. Some cells in mesodermal tissues retain the capacity to differentiate in diverse directions.

Normal Saline—0.9% Sodium Chloride Solution.

"Nucleus Pulposus"—Nucleus pulposus is the gel-like substance in the middle of the spinal disc. It is the remnant of the notochord. It functions to distribute hydraulic pressure in all directions within each disc under compressive loads. The nucleus pulposus consists of large vacuolated notochord cells, small chondrocyte-like cells, collagen fibrils, and proteoglycan aggrecans that aggregate through hyaluronic chains. Attached to each aggrecan molecule are the glycosaminoglycan (GAG) chains of chondroitin sulfate and keratan sulfate. Aggrecan is negatively charged, allowing the nucleus pulposus to attract water molecules. The amount of water and glycosaminoglycans decreases with age and degeneration.

Packing Media—Media used during initial processing and storage of the processed vertebral bodies prior to bone decellularization.

PBS—Phosphate Buffered Saline.

Processing Media—Media used during bone decellularization that may contain DMEM/Low Glucose no phenol red, Human Serum Albumin, Heparin, Gentamicin and DNAse.

"Proteoglycans"—Proteoglycans are proteins that are heavily glycosylated. The basic proteoglycan unit consists of a "core protein" with one or more covalently attached glycosaminoglycan (GAG) chain(s). The point of attachment is a Ser residue to which the glycosaminoglycan is joined through a tetra-saccharide bridge (e.g. chondroitin sulfate-GlcA-Gal-Gal-Xyl-PROTEIN). The Ser residue is generally in the sequence-Ser-Gly-X-Gly- (where X can be any amino acid residue, but Proline), although not every protein with this sequence has an attached glycosaminoglycan. The chains are long, linear carbohydrate polymers that are negatively charged under physiological conditions, due to the occurrence of sulfate and uronic acid groups. Proteoglycans occur in the connective tissue. Proteoglycans are a major component of the animal extracellular matrix, the "filler" substance existing between cells in an organism. Here they form large complexes, both to other proteoglycans, to hyaluronan and to fibrous matrix proteins (such as collagen). They are also involved in binding cations (such as sodium, potassium and calcium) and water, and also regulating the movement of molecules through the matrix. Evidence also shows they can affect the activity and stability of proteins and signaling molecules within the matrix. Individual functions of proteoglycans can be attributed to either the protein core or the attached GAG chain and serve as lubricants.

Quiescence is the reversible state of a cell in which it does not divide but retains the ability to re-enter cell proliferation. Some adult stem cells are maintained in a quiescent state and can be rapidly activated when stimulated, for example by injury to the tissue in which they reside. In broader perspective, quiescence occurs due to lack of nutrition and growth factors whereas senescence takes place due to aging and serious DNA damages . . . . Whereas quiescence (cell cycle arrest) is only one half of the senescence, the other half is growth stimulation which causes actual senescence phenotype.

Senescence: (cell biology) The state of a cell wherein it is no longer capable of dividing although it is still metabolically active and alive. Stem cells may be quiescent and/or senescent, and remain responsive to environmental triggers that activate or encourage phenotypic trajectory based on changing metabolic states in both donor or host biologic systems.

BRIEF DESCRIPTION OF THE DRAWINGS

The invention will be described by way of example and with reference to the accompanying drawings in which.

DETAILED DESCRIPTION OF THE INVENTION

Figure 1:
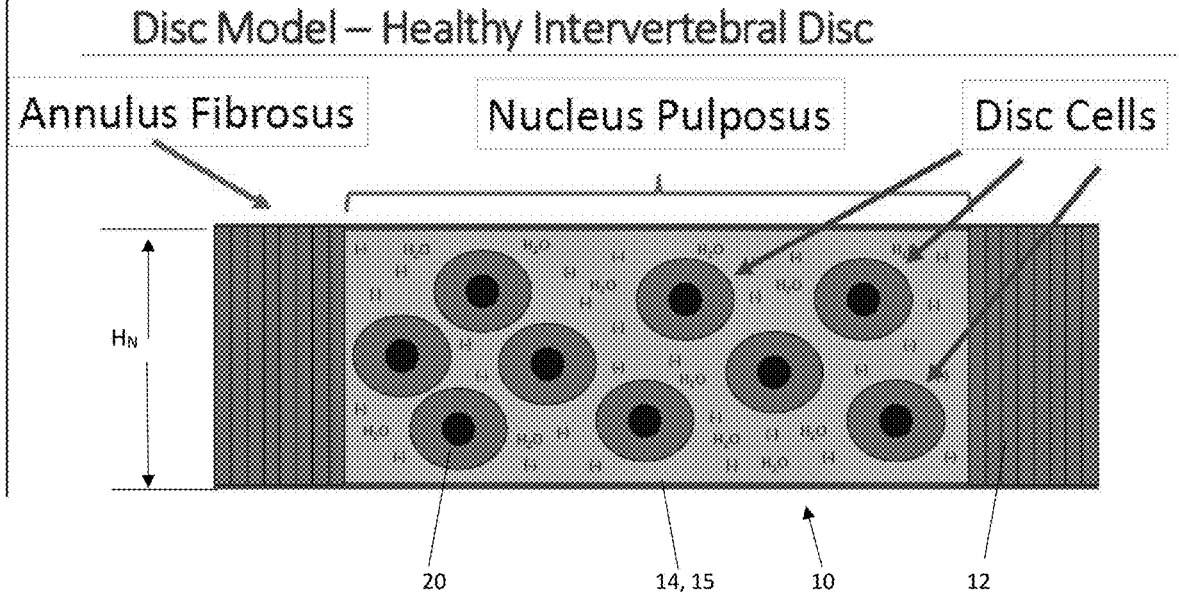
FIG. 1 is a schematic diagram of a cross section depicting a model of a healthy intervertebral disc with the annulus fiber at the peripheral ends and the nucleus pulposus in the central area. The nucleus pulposus schematically showing disc cells dispersed and suspended in water ($H_2O$).

With reference to FIGS. 1 through 7, various schematic views of the present invention are shown. The diagrammatic schematic views depict one embodiment directed to the regenerative repair of an intervertebral disc. This exemplary depiction is only a single representative example. In fact, and as claimed herein, the invention is directed to any degenerative or injured tissue repair wherein the host or patient's cells are exhibiting inflammatory responses. This condition can include bone defects or injury, cartilage damage, nerve damage, organ issues such as the heart, kidneys, pancreas etc.

One of the innovative breakthroughs of the present invention is the use of allograft scaffold matrix which has been seeded and loaded with donor cells that may be quiescent or senescent. These donor senescent and/or quiescent cells react to signals emitted by the host cells, key signals being a broad spectrum of cytokines, growth factors, or exomes that have been consistently paired with inflammation.

An allograft with donor senescent cells is unique in that these allogeneic cells, for all intents and purposes, appear lifeless, or at least unresponsive when procured from donor site. Senescent cells typically are incapable of cell division and thus cannot be readily expanded by culturing through cell division. These cells are not dead and are in fact viable, but are at rest and dormant, incapable of replicating themselves until triggered by the proper signal.

In molecular biology, the culturing and expanding of mesenchymal stem cells has been a key to achieving large quantities of these pluripotent primitive cells in sufficient quantities to be of a therapeutic value. Once collected in sufficient quantities, the cells can be exposed to differentiating factors that align a trajectory based on the appropriate cytokines to which the cells are exposed. In example, agents known for inducing osteoinductivity have been defined that direct cells down an osteogenic lineage towards bone formation. A method of inducing osteogenic differentiation of multi lineage-inducible cells has been shown by culturing the lineage agnostic, but multi-lineage capable cells in an osteogenic medium. One appropriate, and well-established osteogenic medium comprises ascorbic acid 2-phosphate, β-glycerophosphate, and dexamethasone. Osteogenic differentiation often is accounted by demonstrating the expression of Runx2, osteocalcin, collagen I(X1, or bone sialoprotein.

Appropriate cytokines used to pilot cell lineage for cartilage differ from those guiding bone and methods and medium for inducing chondrogenesis might comprise exposure to dexamethasone, TGF-β3, ascorbic acid 2-phosphate, sodium pyruvate, proline, insulin, transferrin, and selenous acid. These descriptions are clearly not intended to provide an exhaustive summary of all possibilities, but to offer methods that have been shown to be effective in phenotypic differentiation of multi-linage inducible cells that are initially lineage agnostic prior to exposure to the methods.

The donor senescent cells can be guided to differentiation by exposure to various allograft scaffold materials such as bone, cartilage, nucleus pulposus, dermis, but until activated remain dormant, at rest and unresponsive. The present invention has discovered that these donor senescent cells, when implanted into a patient, can be activated in response to signaling a condition of the host cells of inflammation. This causes an activation, but not automatically, in fact unless properly preconditioned, the donor senescent cells remain at rest and cannot activate.

The inventors of the present invention found that, if the donor senescent cells were pre-treated with a cryoprotectant of polyampholyte, upon later implantation or injection these donor senescent cells in the allograft will respond to signals from inflamed host cells causing a release of anti-inflammatory cytokines, growth factors and microvesicles including exosomes.

With reference to FIG. 1, a healthy intervertebral disc 10 is illustrated. Around the outer periphery is the annulus fibrosus 12. The annulus fibrosus 12 surrounds the nucleus pulposus 14. The nucleus pulposus 14, as shown, has a vast number of disc cells 20 embedded in the gel like substance in the middle of the spinal disc 10. The nucleus pulposus 14 consists of large vacuolated notochord cells, small chondrocyte-like cells, collagen fibrils, and proteoglycan aggrecans 15 that aggregate through the hydraulic chains. Attached to each aggrecan molecule 15 are glycosaminoglycan (GAG) chains of chondroitin sulfate and keratan sulfate of varying lengths and moiety. Aggrecan 15 is negatively charged, and although depicted in the illustration as floating negative charge in the matrix, the conformation of the molecule is richly structured and through a combination of branched morphology and electro-repulsive forces confers a structured charge which in turn, allows the nucleus pulposus 14 to attract $H_2O$ water molecules. Based on still incomplete understanding of causal and reaction dynamics, enzymes clip the molecules and core proteins, releasing fragments that reduces amount of structured water and subsequently glycosaminoglycans decrease over time with additional degeneration.

Figure 2:
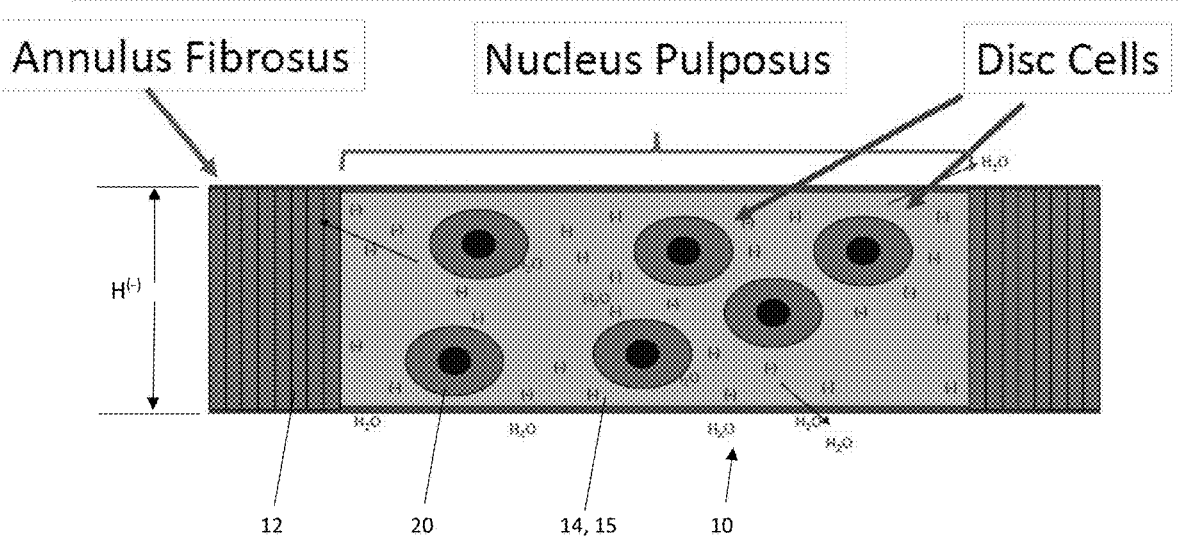
FIG. 2 is a schematic evidencing early disc degeneration as evidenced by few disc cells and loss of water with an associated reduction in disc height in the occurrence of pro-inflammatory cytokines.

As shown in FIG. 1, a healthy intervertebral disc 10 has a height $H_N$, whereas in FIG. 2 depicting an early disc degeneration, the number of disc cells 20 has been greatly reduced. The charge activity and water content in the nucleus pulposus 14 has been also reduced and the height $H^{(-)}$ is reduced as compared to the healthy disc.

Figure 3:
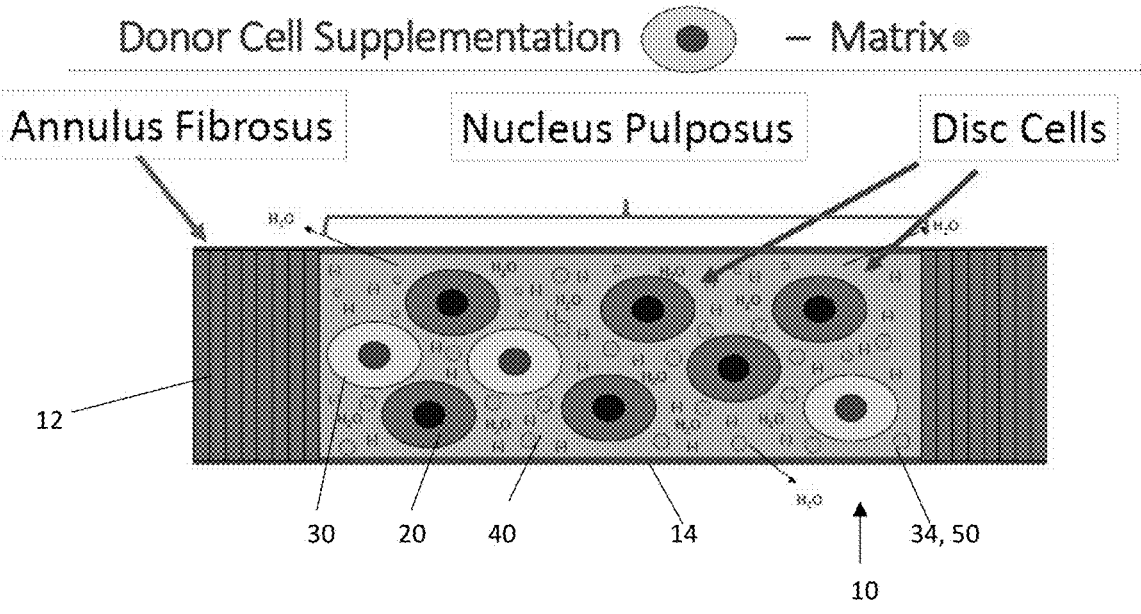
FIG. 3 is a schematic showing donor quiescent and/or senescent cells implanted into a degenerative disc with an allogeneic disc matrix scaffold of nucleus pulposus and normal saline.
Figure 4:
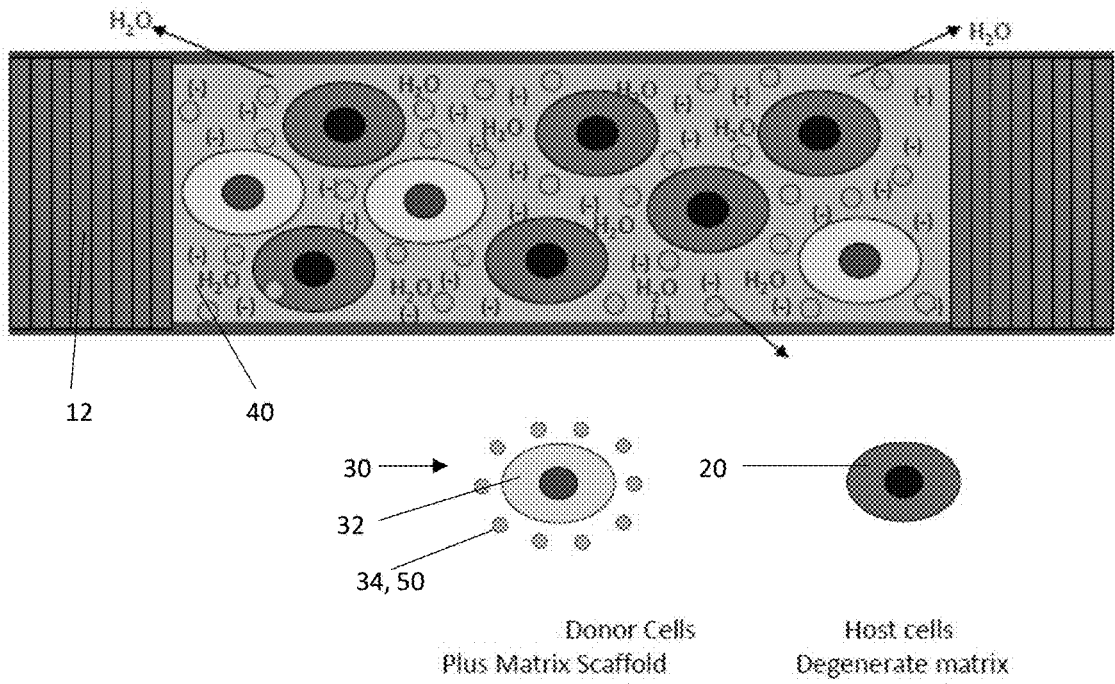
FIG. 4 is an enlarged view of FIG. 3, showing the quiescent and/or senescent donor cells surrounded or suspended in the matrix scaffold on the left below the disc and the host cells exhibiting conditions of inflammation.

As shown in FIGS. 3 and 4, the present invention is used in combination with a degenerative disc or a disc experiencing inflammation. A composition 30 of an allograft scaffold matrix 34 can be inserted into the disc 10. This allograft scaffold matrix 34 includes donor senescent and/or quiescent cells 32 and a cryoprotectant 50 and supplements the depleted volume of the degenerative disc's nucleus pulposus 14. When initially inserted into the disc 10, the composition 30 of allograft scaffold matrix 34 provides additional volume. Preferably, the allograft scaffold matrix 34, in the case of working on a degenerative disc 10, will include a scaffold that has nucleus pulposus particles either micronized or particalized into fibers or small particles. Preferably, the nucleus pulposus is processed from a donor with healthy discs and ground and micronized then freeze-dried. This freeze-dried nucleus pulposus can then be rehydrated with normal saline. Preferably, the mixture is 50 percent nucleus pulposus to 1 cc of normal saline. In addition, disc cells that have been acquired through placental tissue harvesting and manufacturing can be produced. The process is illustrated in U.S. Pat. No. 10,064,896 which is incorporated herein by reference in its entirety.

With the present invention, the composition 30 of allograft scaffold matrix 34 and cryoprotectant 50 has a unique combination of donor senescent cells 32, saline, rehydrated previously freeze-dried nucleus pulposus particles and/or fibers that are preferably reduced to 400 microns or less, more preferably 300 microns or less suitable for direct injection through a 22 gauge needle or cannula. The nucleus pulposus, when injected with the composition 30, will receive the donor senescent cells 32. Importantly, it has been discovered that the senescent cells 32, by themselves without a coating or a treatment with a cryoprotectant 50, remain dormant when injected into a spinal disc. There is virtually no communication, the senescent cells 32 simply occupy space and do not respond to any cell signaling 21 from the host cells 20. However, by applying a cryoprotectant 50 of polyampholyte, preferably ε-poly-L-lysine, a non-glycerol, non DMSO cryoprotectant, which can be injected directly into the patient along with the allograft scaffold matrix 34, it has been determined that this coating 50 causes a field gradient that allows the donor quiescent and/or senescent cells 32 to be able to respond to signals 21 from the host cells 20. When this signaling occurs, the donor quiescent and/or senescent cells 32 are activated causing a release of anti-inflammatory cytokines and microvesicles 31. As shown, this release 31 helps reduce the inflammation of the host cells 20 and helps initiate a repair. In addition, exosomes 40 and other growth factors are released which helps in the regeneration of the degenerative disc 10, as shown in FIGS. 3 and 4.

Figure 5:
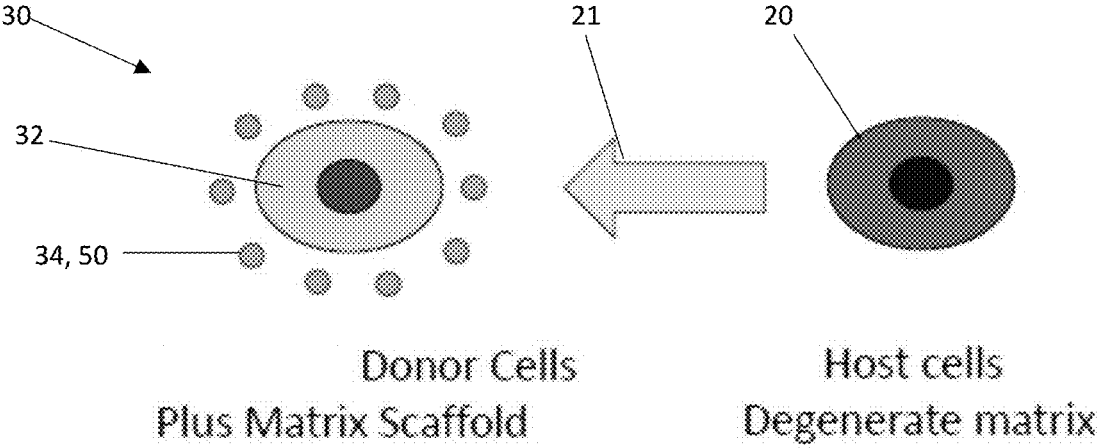
FIG. 5 is a depiction of how the host cells of the degenerative condition signal the implanted quiescent and/or senescent donor cells.

With reference to FIG. 5, the signaling 21 is illustrated from the host cell 20 to the donor quiescent and/or senescent cell 32 plus the scaffold matrix 34 and cryoprotectant 50.

Figure 6:
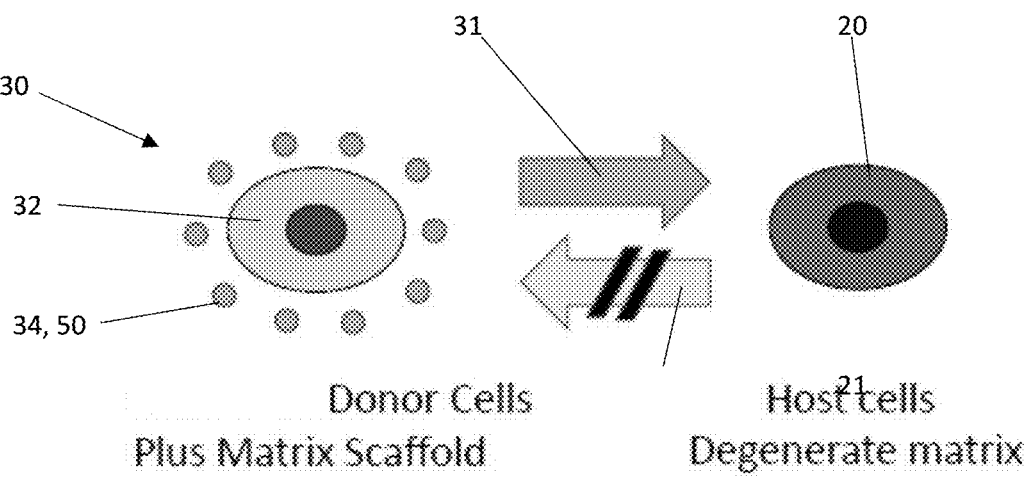
FIG. 6 is a depiction of how the quiescent and/or senescent donor cells respond to the signal of the host cells and activation of the quiescent and/or senescent donor cells to release anti-inflammatory cytokines, growth factor and exosomes to reduce host cell inflammation and rebuild the disc structure by regeneration.

In FIG. 6, the signaling from the pro-inflammatory cytokines in the host cells 20 is dramatically reduced by an anti-inflammatory response 31 sending anti-inflammatory cytokines to the degenerative host cells 20.

Figure 7:
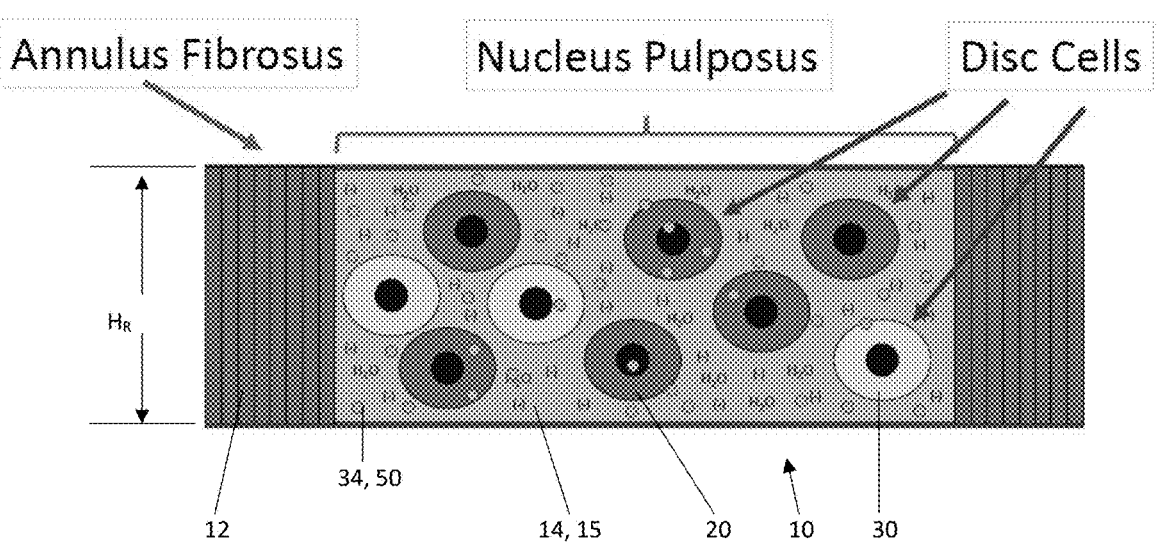
FIG. 7 depicts a restored disc after using a composition made in accordance with the present invention.

With reference to FIG. 7, the restored intervertebral disc 10 is shown. The restored intervertebral disc 10 preferably over a period of 6 months time will have a height $H_R$ that closely approximates a healthy intervertebral disc.

This example of using polyampholyte coated 50 donor quiescent and/or senescent cells 32 in an allograft scaffold matrix 34 when used in the spine, is only one example of the application of the present invention. It is to be understood that these donor senescent cells can also be produced in a scaffold that would allow for bone regeneration. These donor quiescent and/or senescent cells could be used in a fashion similar to that which is described in U.S. Pat. No. 9,675,643 which is incorporated herein by reference in its entirety.

In the use of bone regeneration, the donor quiescent and/or senescent cells can come from bone marrow as described in U.S. Pat. No. 9,675,643. The donor senescent cells will be treated in a similar way to the previously mentioned example for the degenerative disc. They will be treated with a cryoprotectant with a polyampholyte. Once a bone allograft combination is produced this combination can be applied to any bone defect to repair either an injury and/or degenerative condition. Additionally, the scaffold can be mixed with neurological micronized material such as found in U.S. Pat. No. 9,402,869 is neural tissue composition which is incorporated herein by reference in its entirety. The scaffold then would have neural tissue that would activate repair and regeneration of damaged nerves. As can be seen, almost any degenerative condition where inflammation has occurred, is a receptive condition for the use of the present invention which is responsive to the inflammation of the host cells which will allow for a response of the donor quiescent and/or senescent cells in such a way that a regenerative repair of intervertebral disc, bone, cartilage, neurological tissue, ischemic heart and other organs can be accomplished with the use of donor senescent cells that otherwise would be dormant and incapable of providing any reparative response to the host cells.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A biologic composition responsive to inflammation, comprising:

donor quiescent and senescent cells pre-treated with a non-glycerol, non-Dimethyl Sulfoxide (DMSO) cryoprotectant of polyampholyte, wherein the donor quiescent and senescent cells are at rest or dormant; and an allograft scaffold matrix in the form of chips, fibers, or particles or combinations thereof configured for injection or implantation, wherein the allograft scaffold matrix is made of bone, cartilage, nucleus pulposus, or dermis material;

wherein the donor quiescent and senescent cells in the cryoprotectant are seeded onto or loaded into the allograft scaffold matrix.

2. The biologic composition of claim 1, wherein the cryoprotectant is suitable for direct implantation without washing from the allograft scaffold matrix in either a diluted or non-diluted state.

3. The biologic composition of claim 1, wherein the polyampholyte is an ε-poly-L-lysine.

4. The biologic composition of claim 1, wherein the donor quiescent and senescent cells are derived from bone marrow.

5. The biologic composition of claim 1, wherein the donor senescent cells are derived from placental tissue.

6. The biologic composition of claim 1, wherein the allograft scaffold matrix further comprises nucleus pulposus particles or fibers or combinations thereof.

7. The biologic composition of claim 6, wherein the nucleus pulposus particles or fibers have been freeze-dried.

8. The biologic composition of claim 7, wherein the freeze-dried nucleus pulposus particles or fibers have been hydrated in the scaffold matrix with saline.

9. The biologic composition of claim 7, wherein the freeze-dried nucleus pulposus particles or fibers are micronized to be 400 microns or less.

10. The biologic composition of claim 9, wherein the micronized freeze-dried nucleus pulposus particles or fibers are 300 microns or less and suitable for injection via a small gauge lumen or cannula.

11. The biologic composition of claim 10, wherein the small gauge lumen or cannula is a 22-gauge needle.

12. The biologic composition of claim 1, wherein the allograft scaffold matrix in the form of allograft chips, fibers, or particles or combinations thereof comprises mineralized, demineralized, partially demineralized, or combinations of mineralized and demineralized bone chips, bone fibers or bone particles or any combination thereof.

13. The biologic composition of claim 1, wherein the biologic composition reacts to inflammation with a potency and spectral efficiency that exceeds that of a single molecule.

14. The biologic composition of claim 1, wherein the donor quiescent and senescent cells of the biologic composition are derived from one or more of germ cell layers including mesoderm, endoderm, or ectoderm or combinations thereof exhibiting a broad range of phenotypes that are lineage agnostic prior to triggering physiologic events.

15. The biologic composition of claim 1, wherein the donor senescent cells are from a non-marrow derived source and preferably a spine space.

16. The biologic composition of claim 1, wherein the donor quiescent and senescent cells form a heterogenous cell population sufficiently static to remain open to balancing immune response, antigen presentation, cell survival, cell migration, cell differentiation and angiogenesis, such allograft response variable and responsive to broad conditions with multiple separate response to a patient's condition.

17. The biologic composition of claim 1, wherein the donor quiescent and senescent cells are responsive to interspinous or any presented biologic challenge.

18. The biologic composition of claim 1, wherein the chips, fibers, or particles or combinations thereof of the allograft scaffold matrix are of varied shape to allow the donor quiescent and senescent cells in the cryoprotectant to be interposed between the chips, fibers, or particles.

19. The biologic composition of claim 1, wherein the biologic composition is sufficiently stable to protect the anatomy by tissue supplementation while at the same time forming a secretion triggered in the donor quiescent and senescent cells in response to the signal of inflammation.

20. A method of treating a degenerative condition, comprising:

implanting the biologic composition of claim 1 into a degenerated area exhibiting inflammation;

exposing the donor quiescent and senescent cells to signaling from host cells indicating inflammation; and allowing the donor senescent cells to secrete anti-inflammatory cytokines and to secrete appropriate exosomes, thereby reducing inflammation and initiating regeneration of the degenerated area.

21. The method of claim 20, wherein the exposure of the donor senescent cells to the signaling initiates a balancing biological exchange between anabolic and catabolic processes.

22. The method of claim 20, wherein the exposure of the donor senescent cells to the signaling causes secretion and exchange of microvesicles, membrane rafts, miRNA, proteins, growth factors, and/or cytokines, and ions appropriate for tissue function.

23. A method of treating and repairing a degenerative intervertebral disc, comprising:

implanting the biologic composition of claim 1, wherein the scaffold matrix is derived from an intervertebral disc, into a degenerative disc exhibiting inflammation; wherein the step of implanting exposes the donor senescent cells to receive signaling from host cells indicating inflammation; and allowing the donor senescent cells to secrete anti-inflammatory cytokines and exosomes to reduce inflammation and to initiate regeneration of nucleus pulposus of the degenerative disc.

24. The method of claim 23, wherein the exposure of the donor senescent cells to the signaling initiates a balancing biological exchange between anabolic and catabolic.

25. The method of claim 23, wherein the exposure of the donor senescent cells to the signaling causes secretion and exchange of microvesicles, membrane rafts, miRNA, proteins, growth factors, and/or cytokines.

\* \* \* \* \*